(12) United States Patent
DeBates et al.

(10) Patent No.: US 11,806,540 B2
(45) Date of Patent: Nov. 7, 2023

(54) SYSTEMS AND METHODS FOR MANAGING REMOTE THERAPY SESSIONS

(71) Applicant: Advanced Neuromodulation Systems, Inc., Plano, TX (US)

(72) Inventors: Scott DeBates, Frisco, TX (US); Germinal Ibarrola, Prosper, TX (US); Doug Lautner, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 86 days.

(21) Appl. No.: 17/065,176

(22) Filed: Oct. 7, 2020

(65) Prior Publication Data

US 2022/0105350 A1    Apr. 7, 2022

(51) Int. Cl.
*A61N 1/372*    (2006.01)
*A61N 1/36*    (2006.01)

(52) U.S. Cl.
CPC ....... *A61N 1/37264* (2013.01); *A61N 1/3605* (2013.01); *A61N 1/37258* (2013.01); *A61N 1/37282* (2013.01)

(58) Field of Classification Search
CPC ............ A61N 1/37211; A61N 1/37223; A61N 1/37252; A61N 1/37264; A61N 1/37276; A61N 1/37258
See application file for complete search history.

(56) References Cited

U.S. PATENT DOCUMENTS

| | | | |
|---|---|---|---|
| 2006/0030903 A1* | 2/2006 | Seeberger | A61N 1/37223 607/60 |
| 2010/0056941 A1 | 3/2010 | Henke et al. | |
| 2011/0172740 A1* | 7/2011 | Matos | A61N 1/37258 607/60 |
| 2015/0165209 A1 | 6/2015 | Grandhe et al. | |
| 2015/0206408 A1* | 7/2015 | LaLonde | A61B 5/349 340/539.12 |
| 2017/0050035 A1* | 2/2017 | Gupta | A61N 1/37264 |
| 2017/0080234 A1 | 3/2017 | Gillespie et al. | |
| 2017/0165485 A1 | 6/2017 | Sullivan et al. | |
| 2018/0193652 A1 | 7/2018 | Srivastava et al. | |
| 2019/0151659 A1 | 5/2019 | Mishra et al. | |
| 2019/0184167 A1 | 6/2019 | Vansickle et al. | |
| 2019/0223782 A1 | 7/2019 | Wen et al. | |
| 2019/0329042 A1 | 10/2019 | DiLorenzo | |
| 2020/0197711 A1* | 6/2020 | Schilling | H04Q 9/00 |

OTHER PUBLICATIONS

International Search Report and Written Opinion, PCT/US2021/053603, dated Jan. 25, 2022, 13 pages.

* cited by examiner

*Primary Examiner* — George R Evanisko

(74) *Attorney, Agent, or Firm* — Armstrong Teasdale LLP

(57) ABSTRACT

The present disclosure provides systems and methods for managing communications in a remote therapy system. A method includes initiating a remote therapy session by establishing communications between a patient device and an implantable medical device implanted in a patient, and establishing communications between the patient device and a clinician device, determining, using the patient device, a distance between the patient and the patient device, comparing, using the patient device, the determined distance to a threshold distance, and managing the communications between the patient device and the implantable medical device based on the comparison.

18 Claims, 4 Drawing Sheets

SYSTEMS AND METHODS FOR MANAGING REMOTE THERAPY SESSIONS

A. FIELD OF THE DISCLOSURE

The present disclosure relates generally to remote therapy, and more particularly to monitoring and managing communications between a patient device and an implantable medical device during a remote therapy session.

B. BACKGROUND ART

Implantable medical devices have changed how medical care is provided to patients having a variety of chronic illnesses and disorders. For example, implantable cardiac devices improve cardiac function in patients with heart disease by improving quality of life and reducing mortality rates. Further, types of implantable neurostimulators provide a reduction in pain for chronic pain patients and reduce motor difficulties in patients with Parkinson's disease and other movement disorders. In addition, a variety of other medical devices currently exist or are in development to treat other disorders in a wide range of patients.

Many implantable medical devices and other personal medical devices are programmed by a physician or other clinician to optimize the therapy provided by a respective device to an individual patient. The programming may occur using short-range communication links (e.g., inductive wireless telemetry) in an in-person or in-clinic setting.

However, remote patient therapy is a healthcare delivery method that aims to use technology to manage patient health outside of a traditional clinical setting. It is widely expected that remote patient care may increase access to care and decrease healthcare delivery costs.

In at least some known remote therapy systems, a physician is able to program a patient's implantable medical device remotely. Specifically, an audio or video conference interface is provided between a patient device and a physician device that allows the physician to remotely assess the patient both before and after adjusting the programming of the patient's implantable medical device.

For example, for a patient with an implanted neuromodulation device, the physician may ask the patient to perform various movement and speech activities as part of the assessment. For a movement assessment, the patient may move away from the patient device (e.g., the patient device may be a mobile computing device that is placed in a desktop cradle during the assessment). This enables the remote physician to view the patient while they perform the requested movement activities.

The implantable medical device may be programmed or otherwise adjusted by the physician by securely communicating with the implantable medical device via the patient device (e.g., over a wireless connection between the patient device and the implantable medical device). However, at least one challenge with performing such assessment remotely is that the communication between the implantable medical device and the patient device may be impaired or broken as the patient moves away from the patient device. For example, if the patient moves too far from the patient device, a Bluetooth connection established between the patient device and the implantable medical device may vary in quality or fail entirely. Further, changes in the connection quality may impact power consumption of the patient device and the implantable medical device.

Accordingly, it would be desirable to provide a system that dynamically monitors and manages communications between a patient device and an implantable medical device during remote therapy sessions.

BRIEF SUMMARY OF THE DISCLOSURE

In one embodiment, the present disclosure is directed to a method for managing communications in a remote therapy system. The method includes initiating a remote therapy session by establishing communications between a patient device and an implantable medical device implanted in a patient, and establishing communications between the patient device and a clinician device, determining, using the patient device, a distance between the patient and the patient device, comparing, using the patient device, the determined distance to a threshold distance, and managing the communications between the patient device and the implantable medical device based on the comparison.

In another embodiment, the present disclosure is directed to a computing device for managing communications in a remote therapy system. The computing device includes a memory device, and a processor communicatively coupled to the memory device. The processor is configured to initiate a remote therapy session by establishing communications between a patient device and an implantable medical device implanted in a patient, and establishing communications between the patient device and a clinician device, determine a distance between the patient and the patient device, compare the determined distance to a threshold distance, and manage the communications between the patient device and the implantable medical device based on the comparison.

In yet another embodiment, the present disclosure is directed to non-transitory computer-readable media having computer-executable instructions thereon. When executed by a processor of a computing device, the instructions cause the processor of the computing device to initiate a remote therapy session by establishing communications between a patient device and an implantable medical device implanted in a patient, and establishing communications between the patient device and a clinician device, determine a distance between the patient and the patient device, compare the determined distance to a threshold distance, and manage the communications between the patient device and the implantable medical device based on the comparison.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for managing communications in a remote therapy system. A method includes initiating a remote therapy session by establishing communications between a patient device and an implantable medical device implanted in a patient, and establishing communications between the patient device and a clinician device. The method further includes determining, using the patient device, a distance between the patient and the patient device, comparing, using the patient device, the determined distance to a threshold distance, and managing the communications between the patient device and the implantable medical device based on the comparison.

Figure 1:
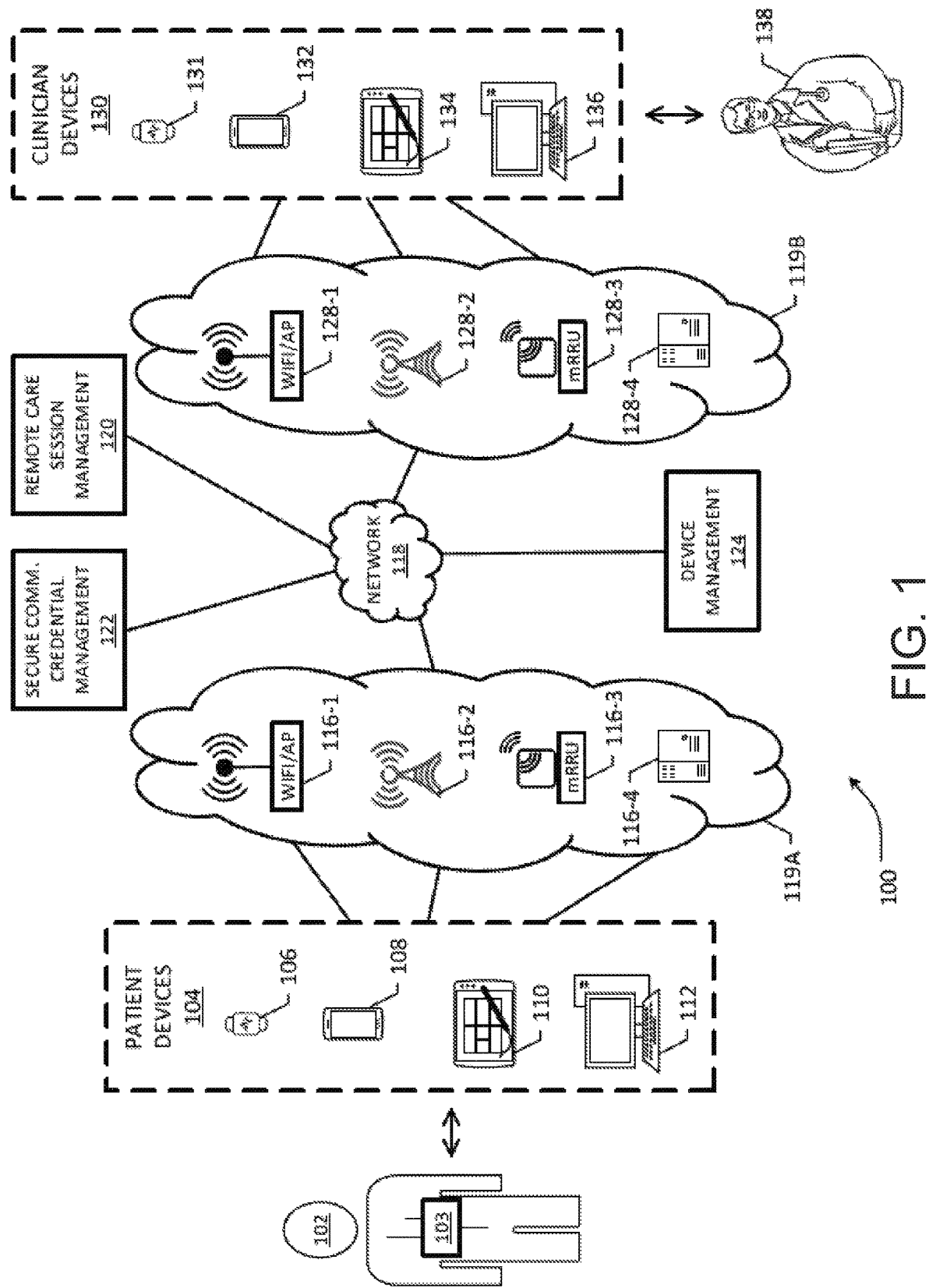
FIG. 1 is a diagram of one embodiment of a network environment for implementing remote therapy sessions.

Referring now to the drawings, and in particular to FIG. 1, a network environment is indicated generally at 100. One or more embodiments of a remote care therapy application or service may be implemented in network environment 100, as described herein. In general, "remote care therapy" may involve any care, biomedical monitoring, or therapy that may be provided by a clinician, a medical professional or a healthcare provider, and/or their respective authorized agents (including digital/virtual assistants), with respect to a patient over a communications network while the patient and the clinician/provider are not in close proximity to each other (e.g., not engaged in an in-person office visit or consultation). Accordingly, in some embodiments, a remote care therapy application may form a telemedicine or a telehealth application or service that not only allows healthcare professionals to use electronic communications to evaluate, diagnose and treat patients remotely, thereby facilitating efficiency as well as scalability, but also provides patients with relatively quick and convenient access to diversified medical expertise that may be geographically distributed over large areas or regions, via secure communications channels as described herein.

Network environment 100 may include any combination or sub-combination of a public packet-switched network infrastructure (e.g., the Internet or worldwide web, also sometimes referred to as the "cloud"), private packet-switched network infrastructures such as Intranets and enterprise networks, health service provider network infrastructures, and the like, any of which may span or involve a variety of access networks, backhaul and core networks in an end-to-end network architecture arrangement between one or more patients, e.g., patient(s) 102, and one or more authorized clinicians, healthcare professionals, or agents thereof, e.g., generally represented as caregiver(s) or clinician(s) 138.

Example patient(s) 102, each having a suitable implantable device 103, may be provided with a variety of corresponding external devices for controlling, programming, otherwise (re)configuring the functionality of respective implantable medical device(s) 103, as is known in the art. Such external devices associated with patient(s) 102 are referred to herein as patient devices 104, and may include a variety of user equipment (UE) devices, tethered or untethered, that may be configured to engage in remote care therapy sessions. By way of example, patient devices 104 may include smartphones, tablets or phablets, laptops/desktops, handheld/palmtop computers, wearable devices such as smart glasses and smart watches, personal digital assistant (PDA) devices, smart digital assistant devices, etc., any of which may operate in association with one or more virtual assistants, smart home/office appliances, smart TVs, virtual reality (VR), mixed reality (MR) or augmented reality (AR) devices, and the like, which are generally exemplified by wearable device(s) 106, smartphone(s) 108, tablet(s)/phablet(s) 110 and computer(s) 112. As such, patient devices 104 may include various types of communications circuitry or interfaces to effectuate wired or wireless communications, short-range and long-range radio frequency (RF) communications, magnetic field communications, Bluetooth communications, etc., using any combination of technologies, protocols, and the like, with external networked elements and/or respective implantable medical devices 103 corresponding to patient(s) 102.

With respect to networked communications, patient devices 104 may be configured, independently or in association with one or more digital/virtual assistants, smart home/premises appliances and/or home networks, to effectuate mobile communications using technologies such as Global System for Mobile Communications (GSM) radio access network (GRAN) technology, Enhanced Data Rates for Global System for Mobile Communications (GSM) Evolution (EDGE) network (GERAN) technology, 4G Long Term Evolution (LTE) technology, Fixed Wireless technology, $5^{th}$ Generation Partnership Project (5GPP or 5G) technology, Integrated Digital Enhanced Network (IDEN) technology, WiMAX technology, various flavors of Code Division Multiple Access (CDMA) technology, heterogeneous access network technology, Universal Mobile Telecommunications System (UMTS) technology, Universal Terrestrial Radio Access Network (UTRAN) technology, All-IP Next Generation Network (NGN) technology, as well as technologies based on various flavors of IEEE 802.11 protocols (e.g., WiFi), and other access point (AP)-based technologies and microcell-based technologies such as femtocells, picocells, etc. Further, some embodiments of patient devices 104 may also include interface circuitry for effectuating network connectivity via satellite communications. Where tethered UE devices are provided as patient devices 104, networked communications may also involve broadband edge network infrastructures based on various flavors of Digital Subscriber Line (DSL) architectures and/or Data Over Cable Service Interface Specification (DOCSIS)-compliant Cable Modem Termination System (CMTS) network architectures (e.g., involving hybrid fiber-coaxial (HFC) physical connectivity). Accordingly, by way of illustration, an edge/access network portion 119A is exemplified with elements such as WiFi/AP node(s) 116-1, macro/microcell node(s) 116-2 and 116-3 (e.g., including micro remote radio units or RRUs, base stations, eNB nodes, etc.) and DSL/CMTS node(s) 116-4.

Similarly, clinicians 138 may be provided with a variety of external devices for controlling, programming, otherwise (re)configuring or providing therapy operations with respect to one or more patients 102 mediated via respective implantable medical device(s) 103, in a local therapy session and/or remote therapy session, depending on implementation and use case scenarios. External devices associated with clinicians 138, referred to herein as clinician devices 130, may include a variety of UE devices, tethered or untethered, similar to patient devices 104, which may be configured to engage in remote care therapy sessions as will be set forth in detail further below. Clinician devices 130 may therefore also include devices (which may operate in association with one or more virtual assistants, smart home/office appliances, VRAR virtual reality (VR) or augmented reality (AR) devices, and the like), generally exemplified by wearable device(s) 131, smartphone(s) 132, tablet(s)/phablet(s) 134 and computer(s) 136. Further, example clinician devices 130 may also include various types of network communications circuitry or interfaces similar to that of patient device 104, which may be configured to operate with a broad range of technologies as set forth above. Accordingly, an edge/access network portion 119B is exemplified as having elements such as WiFi/AP node(s) 128-1, macro/microcell node(s)

128-2 and 128-3 (e.g., including micro remote radio units or RRUs, base stations, eNB nodes, etc.) and DSL/CMTS node(s) 128-4. It should therefore be appreciated that edge/access network portions 119A, 119B may include all or any subset of wireless communication means, technologies and protocols for effectuating data communications with respect to an example embodiment of the systems and methods described herein.

In one arrangement, a plurality of network elements or nodes may be provided for facilitating a remote care therapy service involving one or more clinicians 138 and one or more patients 102, wherein such elements are hosted or otherwise operated by various stakeholders in a service deployment scenario depending on implementation (e.g., including one or more public clouds, private clouds, or any combination thereof). In one embodiment, a remote care session management node 120 is provided, and may be disposed as a cloud-based element coupled to network 118, that is operative in association with a secure communications credentials management node 122 and a device management node 124, to effectuate a trust-based communications overlay/tunneled infrastructure in network environment 100 whereby a clinician may advantageously engage in a remote care therapy session with a patient.

In the embodiments described herein, implantable medical device 103 may be any suitable medical device. For example, implantable medical device may be a neurostimulation device that generates electrical pulses and delivers the pulses to nervous tissue of a patient to treat a variety of disorders.

One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) for the treatment of chronic pain and similar disorders.

Neurostimulation systems generally include a pulse generator and one or more leads. A stimulation lead includes a lead body of insulative material that encloses wire conductors. The distal end of the stimulation lead includes multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Although implantable medical device 103 is described in the context of a neurostimulation device herein, those of skill in the art will appreciate that implantable medical device 103 may be any type of implantable medical device.

As part of a remote therapy session implemented using network environment 100, clinician 138 may request that patient 102 perform various activities (e.g., movement and/or speech activities) as part of an assessment. To perform these activities, patient 102 may move away from patient device 104 (e.g., patient device 104 may be placed in a desktop cradle during the assessment). This enables clinician 138 to view patient 102, but may cause connectivity between implantable medical device 103 and patient device 104 to be impaired or broken as patient 102 moves away from patient device 104. For example, if patient 102 moves too far from patient device 104, a Bluetooth connection established between patient device 104 and implantable medical device 103 may vary in quality or fail entirely. Further, changes in the connection quality may impact power consumption of patient device 104 and implantable medical device 103.

To address these issues, the embodiments described herein provide dynamically monitor and manage communications between patient device 104 and implantable medical device 103 during remote therapy sessions to improve performance.

Specifically, the systems and methods described herein use data from patient device 104 to determine a proximity of patient 102 to patient device 104, and selectively connect and disconnect patient device 104 and implantable medical device 103 based on the determined proximity, as described herein. The systems and methods described herein also facilitate notifying clinician 138 of the connection status between patient device 104 and implantable medical device 103.

Figure 2:
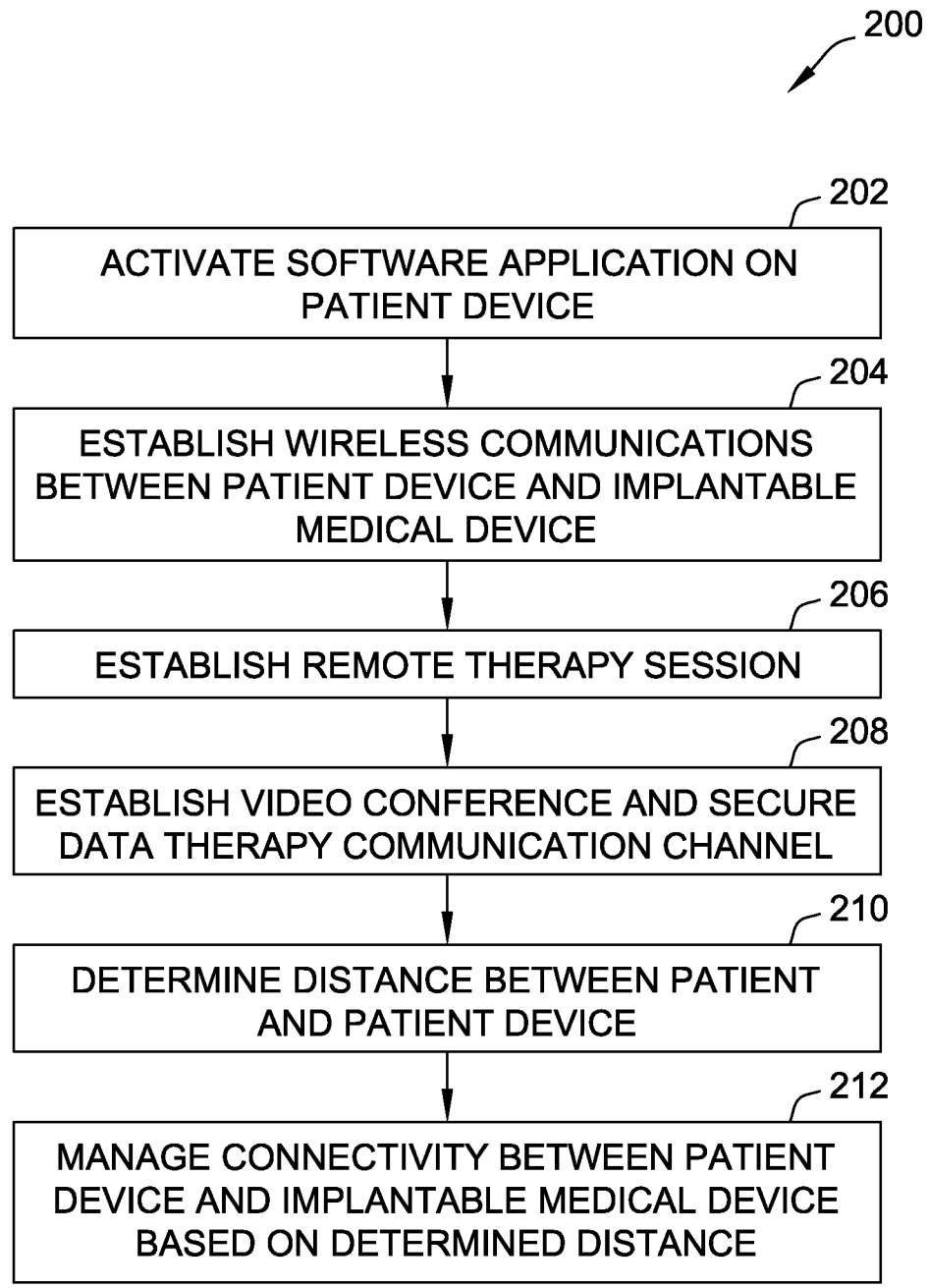
FIG. 2 is a flow diagram of one embodiment of a method for establishing communications between a patient device and an implantable medical device.

FIG. 2 is a flow diagram of an example method 200 for establishing communications between a patient device and an implantable medical device (such as patient device 104 and implantable medical device 103 shown in FIG. 1). In one embodiment, method 200 is implemented using patient device 104 (e.g., via a software application installed on patient device 104). Alternatively, method 200 may be implemented using any suitable computing device.

At block 202, patient 102 activates a software application on patient device 104. Using the software application, patient device 104 establishes wireless communications between patient device 104 and implantable medical device 103 at block 204. Further, at block 206, a remote therapy session is established (e.g., by establishing communications between patient device 104 and clinician device 130).

As part of the remote therapy session, clinician 138 is able to view patient 102 via communications between clinician device 130 and patient device 104. Further, the remote therapy session enables clinician 138 to remotely program implantable medical device 103 via communications between clinician device 130, patient device 104, and implantable medical device 103.

In one embodiment, as part of the remote therapy session, a video conference and secure data therapy communication channel are established between patient device 104 and clinician device 130 at block 208. With the video conference established, at block 210, patient device 104 determines a distance between patient 102 and patient device 104, as described in detail herein. Further, at block 212, patient device 104 (e.g., using the software application), manages connectivity between patient device and implantable medical device 103, as described in detail herein.

Figure 3:
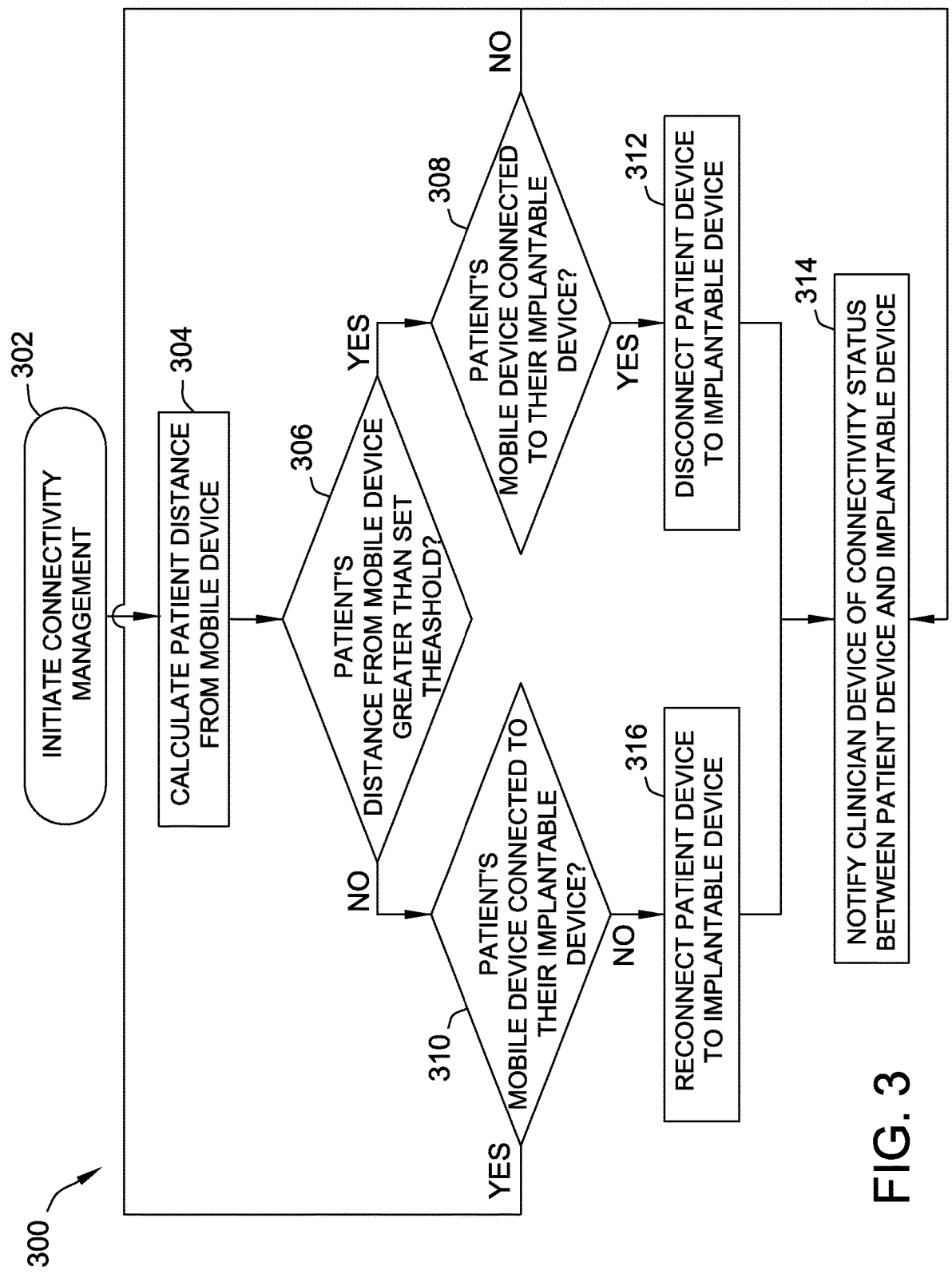
FIG. 3 is a flow diagram of one embodiment of a method for managing connectivity between a patient device and an implantable medical device.

FIG. 3 is a flow diagram of an example method 300 for managing connectivity between a patient device and an implantable medical device (such as patient device 104 and implantable medical device 103 shown in FIG. 1). In one embodiment, method 300 is implemented using patient device 104 (e.g., via a software application installed on patient device 104). Alternatively, method 300 may be implemented using any suitable computing device. Method 300 may be performed periodically (e.g., every 30 seconds) to dynamically manage the connectivity.

At block 302, patient device 104 initiates connectivity management (e.g., via the software application). At block 304, a distance of patient 102 from patient device 104 is calculated (e.g., to determine a distance across which implantable medical device 103 must communicate with patient device 104).

The distance between patient 103 and patient device 104 may be calculated using a number of different techniques. In one example, patient device 104 includes a depth sensor (e.g., implemented using an infrared sensor and/or a facial recognition sensor), and patient device 104 uses the depth sensor to calculate the distance. Alternatively, patient device 104 may use sonar or lidar to calculate the distance (e.g., by emitting signals and calculating the distance based on time of flight of return signals). In another example, patient device 104 may use other video and/or audio sensors to calculate the distance.

For example, in one embodiment, the distance is calculated using the following Equation 1 (e.g., for an image displayed on patient device 104):

$$\text{Distance to object} = (\text{focal length} * \text{patient height} * \text{image height}) / (\text{object height} * \text{sensor height}) \quad \text{Equation 1}$$

where 'focal length' is the focal length of a camera on patient device 104 that acquired the image (e.g., in millimeters (mm)), 'patient height' is the height of patient 102 (e.g., in mm), 'image height' is the height of the displayed image on patient device 104 (e.g., in pixels), 'object height' is the height of the top most pixel of the patient in the image (e.g., in pixels), and 'sensor height' is the height of the camera on patient device 104 (e.g., in mm). For example, if the displayed image is 1440×2560 pixels (width×height), and the top of the patient's head is located at width pixel 740 and height pixel 2000, the image height would be 2560 in portrait mode (1440 in landscape mode), and the object height would be 2000.

Values for the variables in Equation 1 may be determined from a look up table stored on patient device 104, from performing image analysis on an image acquired using patient device 104, and/or from user input provided to patient device 104.

In yet another example, the distance between patient 102 and patient device 104 may be determined using a wearable device worn by patient 102. For example, patient 102 may wear a wearable device (e.g., a smart watch) that calculates a number of steps patient 102 takes when walking away from patient device 104, and the wearable device may transmit the calculated number of steps to patient device 104 for patient device 104 to use in calculating the distance. Those of skill in the art will appreciate that other suitable techniques may also be used to calculate the distance.

At block 306, patient device 104 compares the calculated distance to a threshold distance (e.g., a predetermined threshold distance stored on patient device 104). The threshold distance may be, for example, 10 feet. Alternatively, the threshold distance may be any suitable distance.

If the calculated distance is greater than the threshold distance, flow proceeds to block 308. If the calculated distance is not greater than the threshold distance, flow proceeds to block 310.

At block 308, patient device 104 determines whether patient device 104 is currently communicatively coupled to implantable medical device 103. If patient device 104 is currently communicatively coupled to implantable medical device 103, flow proceeds to block 312, and patient device 104 automatically disconnects from implantable medical device 103 to terminate communications. If patient device 104 is not currently communicatively coupled to implantable medical device 103, flow proceeds to block 314.

At block 310, patient device 104 determines whether patient device 104 is currently communicatively coupled to implantable medical device 103. If patient device 104 is currently communicatively coupled to implantable medical device 103, flow proceeds to block 314. If patient device 104 is not currently communicatively coupled to implantable medical device 103, flow proceeds to block 316, and patient device 104 automatically reconnects to implantable medical device 103 to reestablish communications.

From both block 312 and 316, flow proceeds to block 314. At block 314, patient device 104 notifies clinician device 130 of the connectivity status between patient device 104 and implantable medical device 103. For example, patient device 104 may transmit a message to clinician device 130 that causes clinician device to display the connectivity status to clinician 138. This apprises clinician 138 of the connectivity status, and enables clinician 138 to proceed appropriately. For example, if clinician 138 intends to remotely program implantable medical device 103, clinician can wait until the connectivity status indicates patient device 104 is currently communicatively coupled to implantable medical device 103 before proceeding.

In some embodiments, patient 102 is also apprised of the connectivity status. For example, in one embodiment, patient device 104 generates an audio and/or visual alert that indicates the connectivity status, and that is observable by patient 102. In another embodiment, patient device 104 uses implantable medical device 103 to inform patient 102 of the connectivity status. For example, prior to disconnecting, patient device 104 may send a signal to implantable medical device 103 that causes implantable medical device 103 to generate an alert (e.g., by vibrating and/or emitting a sound) that notifies patient 102 that the connection is relatively weak and will be terminated.

In some embodiments, the power consumption of implantable medical device 103 and/or patient device 104 may be managed. For example, when the calculated distance is greater than the threshold distance, a power level of implantable medical device 103 and/or patient device 104 may be increased in an attempt to prevent a communications failure.

For example, in one embodiment, the received signal strength indication (RSSI) level and the occurrence of data re-transmission may be monitored. When data re-transmission is occurring and/or the RSSI level is relatively poor (e.g., approximately 95 dB), the power level (e.g., the power level of a Bluetooth antenna power amplifier in implantable medical device 103 and/or patient device 104) may be increased to allowed for continued communications, even when implantable medical device 103 and/or patient device 104 are relatively far apart. In contrast, when implantable medical device 103 and/or patient device 104 are relatively close, such that data re-transmissions are not occurring and/or the RSSI level is relatively strong (e.g., approximately 55 dB), the power level is decreased. Adjusting the power amplification based on distance enables realizing battery power efficiencies for implantable medical device 103 and patient device 104.

Figure 4:
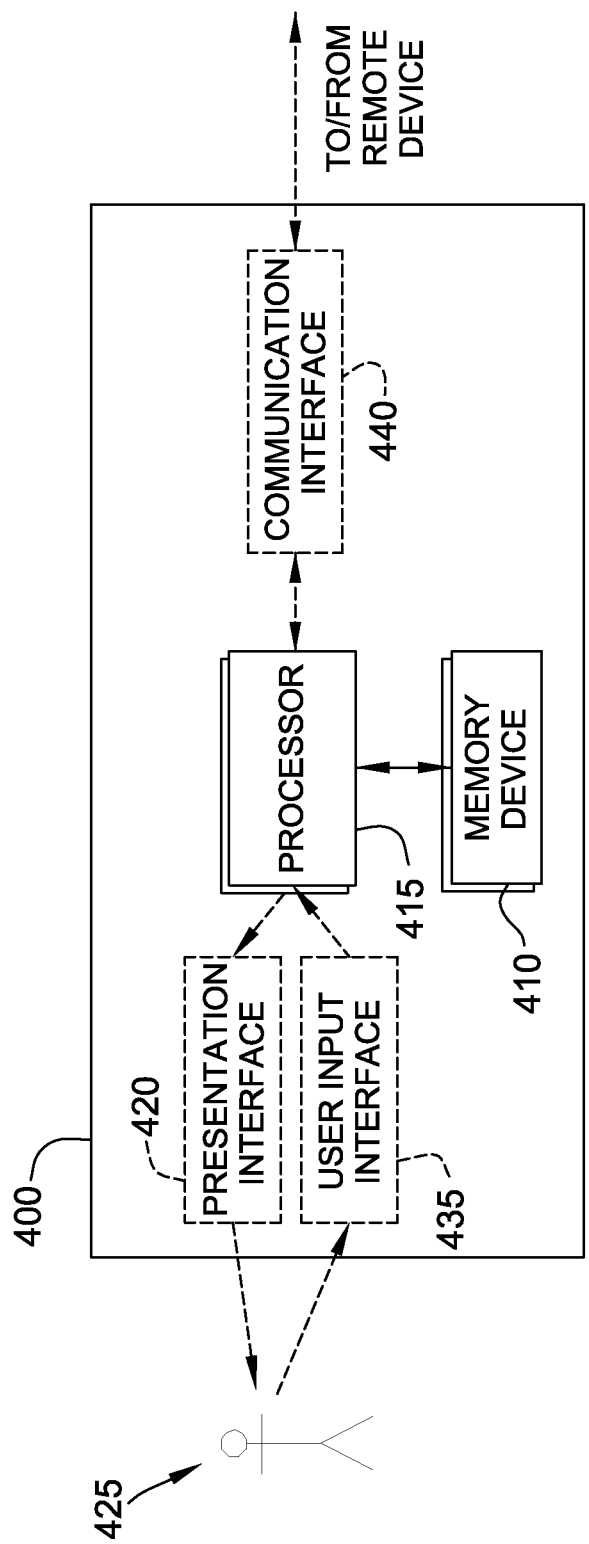
FIG. 4 is a block diagram of one embodiment of a computing device.

FIG. 4 illustrates one embodiment of a computing device 400 that may be used to implement the systems and methods described herein. For example, computing device 400 may be used to implement patient device 104 and/or clinician device 130 (bot shown in FIG. 1).

Computing device 400 includes at least one memory device 410 and a processor 415 that is coupled to memory device 410 for executing instructions. In some embodiments, executable instructions are stored in memory device 410. In this embodiment, computing device 400 performs one or more operations described herein by programming processor 415. For example, processor 415 may be programmed by encoding an operation as one or more executable instructions and by providing the executable instructions in memory device 410.

Processor 415 may include one or more processing units (e.g., in a multi-core configuration). Further, processor 415 may be implemented using one or more heterogeneous processor systems in which a main processor is present with secondary processors on a single chip. In another illustrative example, processor 415 may be a symmetric multi-processor system containing multiple processors of the same type. Further, processor 415 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. In one embodiment, processor 415 is a GPU (as opposed to a central processing unit (CPU)). Alternatively, processor 415 may be any processing device capable of implementing the systems and methods described herein.

In this embodiment, memory device 410 is one or more devices that enable information such as executable instructions and/or other data to be stored and retrieved. Memory device 410 may include one or more computer readable media, such as, without limitation, dynamic random access memory (DRAM), static random access memory (SRAM), a solid state disk, and/or a hard disk. Memory device 410 may be configured to store, without limitation, application source code, application object code, source code portions of interest, object code portions of interest, configuration data, execution events and/or any other type of data. In one embodiment, memory device 410 is a GPU memory unit. Alternatively, memory device 410 may be any storage device capable of implementing the systems and methods described herein.

In this embodiment, computing device 400 includes a presentation interface 420 that is coupled to processor 415. Presentation interface 420 presents information to a user 425 (e.g., patient 102 or physician 138). For example, presentation interface 420 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 420 includes one or more display devices.

In this embodiment, computing device 400 includes a user input interface 435. User input interface 435 is coupled to processor 415 and receives input from user 425. User input interface 435 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 420 and user input interface 435.

Computing device 400, in this embodiment, includes a communication interface 440 coupled to processor 415. Communication interface 440 communicates with one or more remote devices. To communicate with remote devices, communication interface 440 may include, for example, a wired network adapter, a wireless network adapter, and/or a mobile telecommunications adapter.

The embodiments described herein provide systems and methods for managing communications in a remote therapy system. A method includes initiating a remote therapy session by establishing communications between a patient device and an implantable medical device implanted in a patient, and establishing communications between the patient device and a clinician device. The method further includes determining, using the patient device, a distance between the patient and the patient device, comparing, using the patient device, the determined distance to a threshold distance, and managing the communications between the patient device and the implantable medical device based on the comparison.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method for managing communications in a remote therapy system, the method comprising:
   initiating a remote therapy session by establishing with communication circuitry communications between a patient device and an implantable medical device implanted in a patient, and establishing communications between the patient device and a clinician device;

sensing and determining, using at least one sensor on the patient device, a distance between the patient and the patient device;

comparing, using the patient device, the determined distance to a threshold distance; and managing the communications between the patient device and the implantable medical device by:

determining that the determined distance is greater than the threshold distance, wherein the patient device is capable of communicating with the implantable medical device at distances greater than the threshold distance;

determining, while the determined distance between the patient and the patient device is greater than the threshold distance, that the implantable medical device is currently communicatively coupled to the patient device; and in response to determining that the implanted medical device is currently communicatively coupled to the patient device while the determined distance between the patient and the patient device is greater than the threshold distance, automatically terminating the communications between the implantable medical device and the patient device.

2. The method of claim 1, wherein managing the communications between the patient device and the implantable medical device further comprises reestablishing the communications between the implantable medical device and the patient device when the determined distance subsequently becomes less than the threshold distance.

3. The method of claim 1, further comprising causing the clinician device to indicate a connectivity status between the patient device and the implantable medical device.

4. The method of claim 1, wherein the implantable medical device is a neuromodulation device.

5. The method of claim 1, wherein managing the communications between the patient device and the implantable medical device further comprises increasing a power level of a wireless communications antenna on at least one of the patient device and the implantable medical device.

6. The method of claim 1, further comprising causing the implantable medical device to generate an alert observable by the patient, the alert indicating a connectivity status between the patient device and the implantable medical device.

7. The method of claim 1, wherein managing the communications further comprises transmitting, prior to automatically terminating the communications between the implantable medical device and the patient device, a signal from the patient device to the implantable medical device that causes the implantable medical device to vibrate or emit a sound.

8. A remote therapy system comprising:

a sensor configured to sense a distance between a patient and a patient device; and communication circuitry for communicating between the patient device and an implantable device; and a computing device for managing communications in the remote therapy system, the computing device communicatively coupled to the sensor and comprising:

a memory device; and a processor communicatively coupled to the memory device, the processor configured to:

initiate a remote therapy session by establishing with the communication circuitry the communications between the patient device and the implantable medical device implanted in the patient, and establishing communications between the patient device and a clinician device;

receive the sensed distance from the sensor;

compare the sensed distance to a threshold distance; and manage the communications between the patient device and the implantable medical device by:

determining that the sensed distance is greater than the threshold distance, wherein the patient device is capable of communicating with the implantable medical device at distances greater than the threshold distance;

determining, while the sensed distance between the patient and the patient device is greater than the threshold distance, that the implantable medical device is currently communicatively coupled to the patient device; and in response to determining that the implanted medical device is currently communicatively coupled to the patient device while the sensed distance between the patient and the patient device is greater than the threshold distance, automatically terminating the communications between the implantable medical device and the patient device.

9. The remote therapy system of claim 8, wherein the computing device comprises the patient device.

10. The remote therapy system of claim 8, wherein to manage the communications between the patient device and the implantable medical device, the processor is further configured to reestablish the communications between the implantable medical device and the patient device when the sensed distance is less than the threshold distance and the implantable medical device is not currently communicatively coupled to the patient device.

11. The remote therapy system of claim 8, wherein the processor is further configured to cause the clinician device to indicate a connectivity status between the patient device and the implantable medical device.

12. The remote therapy system of claim 8, wherein to manage the communications between the patient device and the implantable medical device, the processor is further configured to increase a power level of a wireless communications antenna on at least one of the patient device and the implantable medical device.

13. The remote therapy system of claim 8, wherein the processor is further configured to cause the implantable medical device to generate an alert observable by the patient, the alert indicating a connectivity status between the patient device and the implantable medical device.

14. Non-transitory computer-readable media having computer- executable instructions thereon, wherein when executed by a processor of a computing device, cause the processor of the computing device to:

initiate a remote therapy session by establishing with communication circuitry communications between a patient device and an implantable medical device implanted in a patient, and establishing communications between the patient device and a clinician device;

sense and determine, using at least one sensor on the patient device, a distance between the patient and the patient device;

compare the determined distance to a threshold distance; and manage the communications between the patient device and the implantable medical device by:
- determining that the determined distance is greater than the threshold distance, wherein the patient device is capable of communicating with the implantable medical device at distances greater than the threshold distance;
- determining, while the determined distance between the patient and the patient device is greater than the threshold distance, that the implantable medical device is currently communicatively coupled to the patient device; and
- in response to determining that the implanted medical device is currently communicatively coupled to the patient device while the determined distance between the patient and the patient device is greater than the threshold distance, automatically terminating the communications between the implantable medical device and the patient device.

15. The non-transitory computer-readable media of claim 14, wherein to manage the communications between the patient device and the implantable medical device, the instructions cause the processor to reestablish the communications between the implantable medical device and the patient device when the determined distance is less than the threshold distance and the implantable medical device is not currently communicatively coupled to the patient device.

16. The non-transitory computer-readable media of claim 14, wherein the instructions further cause the processor to cause the clinician device to indicate a connectivity status between the patient device and the implantable medical device.

17. The non-transitory computer-readable media of claim 14, wherein to manage the communications between the patient device and the implantable medical device, the instructions further cause the processor to increase a power level of a wireless communications antenna on at least one of the patient device and the implantable medical device.

18. The non-transitory computer-readable media of claim 14, wherein the instructions further cause the processor to cause the implantable medical device to generate an alert observable by the patient, the alert indicating a connectivity status between the patient device and the implantable medical device.

* * * * *